(12) United States Patent
Miller

(10) Patent No.: US 8,461,489 B2
(45) Date of Patent: Jun. 11, 2013

(54) FURNACE FOR DENTAL PROSTHESIS OR PARTIAL DENTAL PROSTHESIS

(75) Inventor: Stephan Miller, Traunstein (DE)

(73) Assignee: DEKEMA Dental-Keramiköfen GmbH, Freilassing (DE)

( * ) Notice: Subject to any disclaimer, the term of this patent is extended or adjusted under 35 U.S.C. 154(b) by 612 days.

(21) Appl. No.: 12/528,073

(22) PCT Filed: Jan. 25, 2008

(86) PCT No.: PCT/EP2008/000601
§ 371 (c)(1),
(2), (4) Date: Mar. 23, 2010

(87) PCT Pub. No.: WO2008/101583
PCT Pub. Date: Aug. 28, 2008

(65) Prior Publication Data
US 2010/0213185 A1   Aug. 26, 2010

(30) Foreign Application Priority Data
Feb. 21, 2007 (DE) .......................... 10 2007 008 476

(51) Int. Cl.
*F27B 14/00* (2006.01)
(52) U.S. Cl.
USPC .......................................... 219/425; 219/482

(58) Field of Classification Search
USPC ................................. 219/402, 420, 422, 425
See application file for complete search history.

(56) References Cited

U.S. PATENT DOCUMENTS

| 4,597,431 A | 7/1986 | Hobo et al. |
| 6,469,283 B1 | 10/2002 | Burkhart et al. |
| 2003/0234095 A1* | 12/2003 | Usui .............................. 164/336 |
| 2005/0011885 A1 | 1/2005 | Seghatol et al. |
| 2006/0169687 A1 | 8/2006 | Geockner et al. |

FOREIGN PATENT DOCUMENTS

| DE | 34 47 672 A1 | 7/1985 |
| DE | 197 53 837 C2 | 6/1999 |
| GB | 1077021 A | 7/1967 |
| GB | 1153277 A | 5/1969 |
| JP | 2-73413 A | 3/1990 |

* cited by examiner

*Primary Examiner* — Cheung Lee
(74) *Attorney, Agent, or Firm* — Kilpatrick Townsend & Stockton LLP

(57) ABSTRACT

The invention relates to a furnace for a dental prosthesis, or a partial dental prosthesis, comprising a furnace chamber, a plurality of heating elements for heating the furnace chamber, and a power connector for connecting the heating elements to a power grid, wherein means for limiting the power consumption of the furnace are provided in order to increase the application possibilities and improve the furnace performance.

18 Claims, 3 Drawing Sheets

Max U

FURNACE FOR DENTAL PROSTHESIS OR PARTIAL DENTAL PROSTHESIS

CROSS REFERENCE TO RELATED APPLICATIONS

Figure 1:
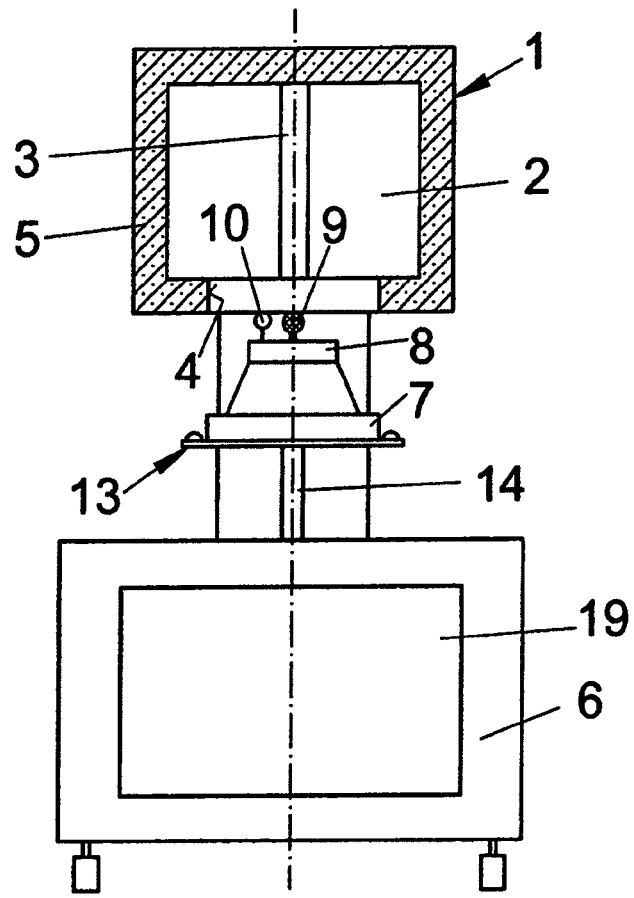

This application is a National Stage of International Application No. PCT/EP2008/000601 filed Jan. 25, 2008 and which claims the benefit of German Patent Application No. 10 2007 008 476.7, the disclosures of all applications being incorporated herein by reference.

The present invention relates to a furnace for a dental prosthesis or a partial dental prosthesis having a firing chamber, a plurality of heating elements for the heating of the firing chamber and a power supply connection for the connection of the heating elements to a mains supply.

Such a furnace is known, for example, from DE 197 53 837. The generation of a high temperature and its maintenance over the firing period is important with such furnaces. An exact regulation of the temperature is required for the quality of the dental prosthesis or of the partial dental prosthesis.

It is the underlying object of the invention to provide a furnace of the named kind which has an increased functionality and delivers good firing results.

This object is satisfied in that means are provided for the restriction of the power consumption of the furnace.

The furnace can be operated at different mains voltages due to the restriction of the power consumption of the furnace. One and the same furnace can therefore be produced for countries with different mains voltages, whereby the manufacturing costs are reduced. In addition, the handling is simplified since the mains voltage does not have to be observed.

Means for the monitoring and for the restriction of the current consumption of the furnace are preferably provided. It can thereby be prevented that too high a current is taken from the mains.

In accordance with a further embodiment of the invention, means are provided for the monitoring and restriction of the voltage effective at the heating elements. Damage to the heating elements through too high a voltage can hereby be prevented.

It is further preferred if means are provided by which the voltage applied to the furnace can be determined, in particular automatically. These means can preferably serve to switch between series connection and parallel connection of the heating elements, in particular automatically, in dependence on the voltage determined. An adaptation to the mains voltage can take place in this manner.

For example, the heating elements can be connected in parallel at a mains voltage applied to the furnace of 115 volts. There is thus a potential drop of 115 volts at each heating element. If, in contrast, the mains voltage is 230 volts, a series connection is preferred. With three heating elements, for example, there is a potential drop of approximately 77 volts at each of them. Generally, the connection is preferably made so that there is a potential drop to the order of approximately 70 to 120 volts at each heating element. This has proved to be advantageous for the operation of the heating elements, in particular heating elements of silicon carbide.

The switch between a parallel connection and a series connection can preferably take place by current bridges. The heating elements can be connected together in the desired manner by plugging in or removing the current bridges. If the switch should, in contrast, take place automatically, at least one relay is preferably used for this purpose.

The current consumed by the furnace is preferably measured by a Hall sensor. This has the advantage that the current measurement can take place potential-free.

In accordance with a further embodiment of the invention, means are provided by which the power consumption and/or the voltage applied at the heating elements can be restricted in dependence on the strength of the heating elements at the currently prevailing temperature or at a maximum temperature of the heating elements. It can be ensured by these means that the heating elements are not destroyed or damaged in operation. This is in particular important with heating elements of silicon carbide since their strength reduces relatively considerably as the temperature increases. In addition, these heating elements have a temperature-dependent resistance, with the dependence being highly non-linear. An increased risk thereby arises that the current consumption of the heating elements becomes too large.

In accordance with an embodiment of the invention, the strength values of the heating elements can be taken from a previously prepared table in which the strength of heating elements from the material used is set forth in dependence on the temperature.

In accordance with a further embodiment of the invention, means are provided by which the power consumption of the furnace is restricted in dependence on a permitted power consumption, in particular a permitted current drain from a mains power supply. It can be ensured by these means that the mains power supply is not overloaded by the furnace.

A leading edge control of an AC voltage applied to the furnace can advantageously be provided for the power restriction. Only specific fractions of the AC voltage are applied to the heating elements in accordance with the desired power consumptions by the leading edge control, whereas the residual portions are fed back into the mains power supply. That is, fractions of the sinus waves delivered by the mains power supply are applied to the heating elements and the remaining portions are returned to the mains. To prevent contamination of the mains, a mains filter can be provided. The resulting voltage and thus the power consumption of the firing elements result from the fraction of the AC voltage applied to the heating elements. A trailing edge control can also be used in the same way.

Another possibility is to use a so-called half-wave control for the power restriction. In this respect, the half-waves of the AC voltage are, on the one hand, divided among the individual heating elements and, on the other hand, individual half-waves can also not be applied to any heating element so that a power reduction likewise results overall. The same applies to the leading edge control or trailing edge control. The fractions of the sinus wave can also be distributed among the individual heating elements here.

Figure 2:
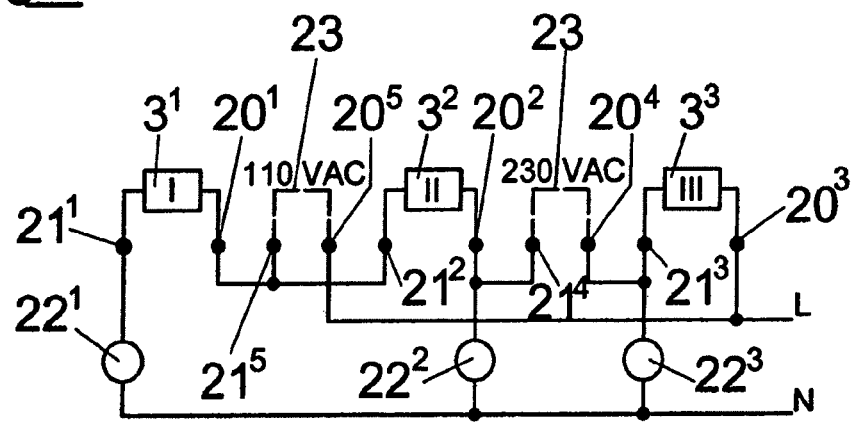
Figure 3:
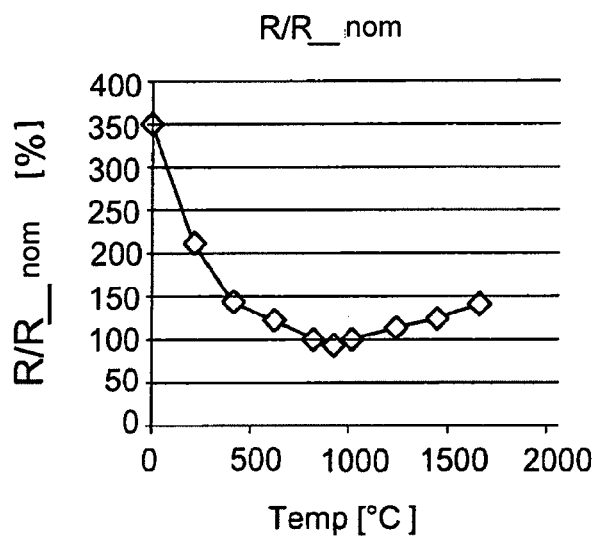
Figure 4:
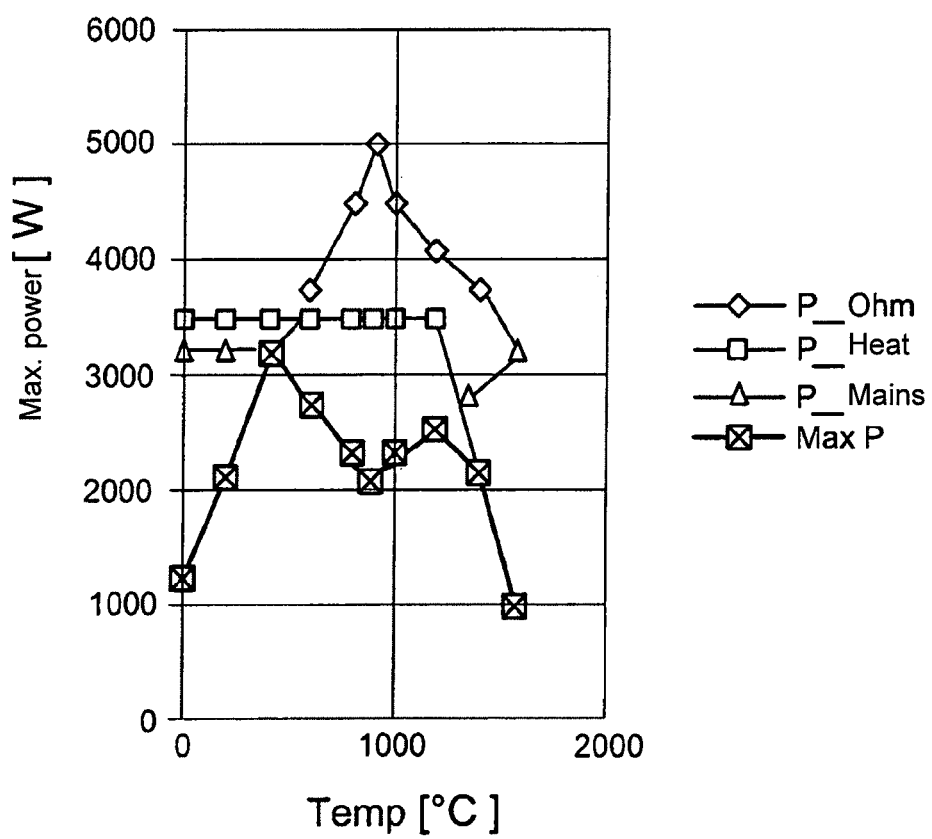
Figure 5:
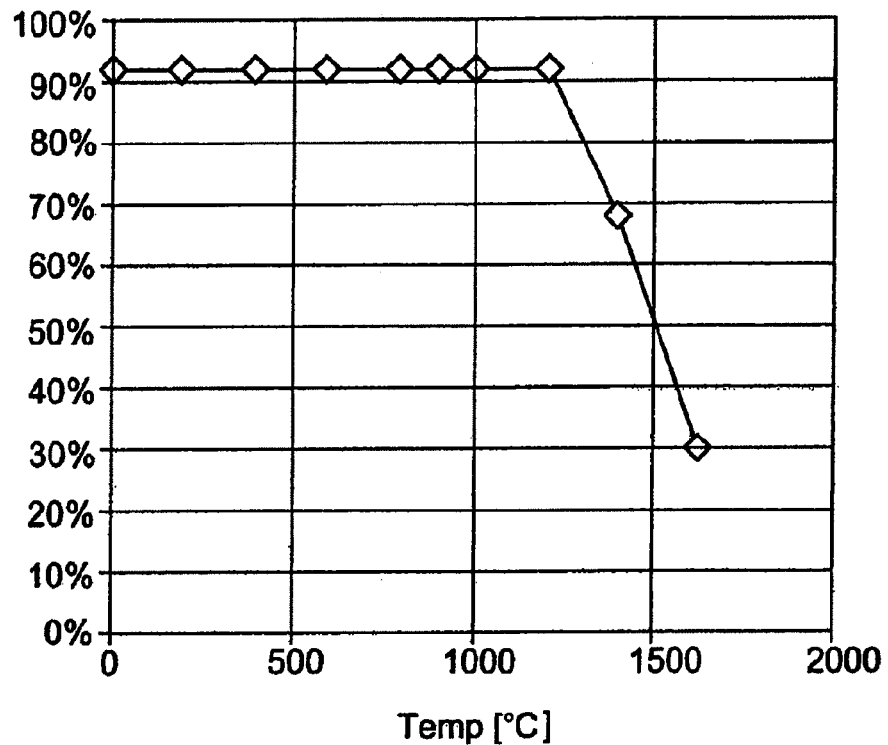
Figure 6:
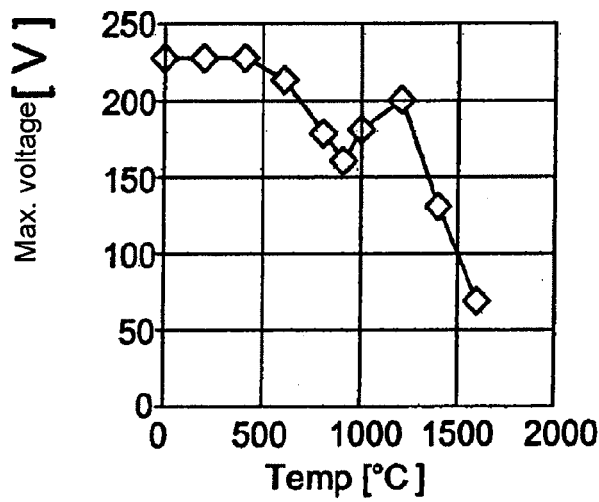

Embodiments of the invention are shown in the drawing and will be described in the following. There are shown, schematically in each case:

FIG. 1 a furnace in accordance with the invention;

FIG. 2 a circuit diagram for a selectively parallel or series connection of heating elements;

FIG. 3 a representation of the temperature dependence of the nominal resistance of a heating body;

FIG. 4 a representation of the maximum powers in a furnace in accordance with the invention;

FIG. 5 a representation of the regulation via half-wave control or leading edge control; and FIG. 6 a representation of the maximum voltage in dependence on the heating element temperature.

The furnace shown in FIG. 1 includes a housing 1 having a firing chamber 2 which can be heated via heating elements 3 and can preferably be evacuated via means which are not shown. The heating elements 3 are made as heating rods and are arranged distributed over the periphery of the firing chamber 2. Three such heating elements 3 are particularly preferably provided.

The firing chamber 2 has an opening 4 at its lower side and is surrounded at all sides, with the exception of the opening 4, by an insulation layer 5, in particular made of fireclay or ceramic fibers. A housing part 6 is present beneath the firing chamber 2 and has a drive mechanism, not shown here, for a lifting plate 13 which supports a firing table 7 and is movable via a rod 14 by the drive apparatus to close and open the firing chamber 2. A firing tray 8 with a firing object 9 arranged thereon is shown on the firing table 7. A thermosensor 10 is present on the firing tray 8 beside the firing object 9.

The housing part 6 includes control means and programming devices for the furnace as well as display means 19. These control means include means for the restriction of the power consumption of the furnace, in particular means for the monitoring and for the restriction of the current consumption and/or of the voltage applied to the heating elements 3. In addition, the voltage effective at the furnace is automatically determined by these means. In dependence on this, this firing elements 3 of the furnace are connected in parallel or in series to preferably reach a voltage in the range from 70 to 120 volts at the heating elements 3. With a mains voltage of, for example, 230 volts, the heating elements 3 are therefore preferably connected in series so that there is a potential drop of approximately 77 volts each heating element. If the mains voltage, in contrast, amounts to 115 volts, for example, the heating elements 3 are connected in parallel so that there is a potential drop of 115 volts at each heating element.

In accordance with an embodiment of the invention, current bridges can be provided for the switching between the parallel and the series connection. A corresponding circuit is shown in FIG. 2. The three heating elements $3^1$, $3^2$ and $3^3$ each have two input terminals $20^1$, $20^2$ and $20^3$ as well as three output terminals $21^1$, $21^2$ and $21^3$. In addition, two further terminal pairs, namely two further input terminals $20^4$ and $20^5$ as well as two further output terminals $21^4$ and $21^5$ are present between the heating elements $3^1$, $3^2$ and $3^3$. Finally, three relays $22^1$, $22^2$ and $22^3$ are associated with the heating elements $3^1$, $3^2$ and $3^3$.

As shown, the input terminal $20^3$ of the third heating element $3^3$ and the input terminal $20^5$ of the second further terminal pair is connected to the load feed line L of the mains supply, whereas the neutral line N of the mains supply is connected to the respective one side of the three relays $22^1$, $22^2$ and $22^3$. The other side of the first and third relays $22^1$ and $22^3$ is respectively connected to the output terminal $21^1$, $21^3$ of the first or third heating elements $3^1$,$3^3$ respectively, whereas the other side of the second relay $22^2$ is connected to the input terminal $20^2$ of the second heating element $3^2$. Finally, the input terminal $20^4$ of the first further terminal pair is connected to the output $21^3$ of the third heating element $3^3$ and the output terminal $21^4$ is connected to the input $20^2$ of the second heating element $3^2$ and the output terminal $21^5$ of the second further terminal pair to the input terminal $20^1$ of the first heating element $3^1$ and to the output terminal $21^2$ of the second heating element $3^2$.

As can be recognized, a series connection or parallel connection of the heating elements $3^1$, $3^2$ and $3^3$ can be realized by a selective insertion of a current bridge 25, shown chain-dotted here, into the first further terminal pair $20^4$, $21^4$ or into the second further terminal pair $20^5$, $21^5$. As can furthermore be recognized, the three heating elements $3^1$, $3^2$ and $3^3$ are operated via only one power relay $22^1$ with a series connection, but in contrast via all three power relays $22^1$, $22^2$ and $22^3$ with a parallel connection. With a series connection, all three heating elements $3^1$, $3^2$ and $3^3$ are therefore controlled together, whereas an individual control is possible with a parallel, circuit.

Another possibility is to replace the bridge 23 by two additional relays. An automatic switchover can thus be realized between the series connection and the parallel connection. In both cases, the series connection is preferably used at a mains voltage of 230 volts and the parallel connection at a mains voltage of 115 volts. Alternatively, a relay with two changers can also be used. Since the relays are not switched over under load, the maximum switching cycles do not play any role.

As stated, the power consumption, in particular the current consumption, can be restricted by the control of the furnace in accordance with the invention. A power restriction is necessary because the heating elements, in particular heating elements made of silicon carbide, have a non-linear, temperature-dependent resistance. Furthermore, the heating elements also have temperature-dependent mechanical load limits. Finally, the maximum power output in dependence on the mains may not be exceeded. The maximum heating rate is thus also mains-dependent. A Hall sensor preferably serves for the determination of the current consumption by the heating elements.

A half-wave control, alternatively a leading edge control or a trailing edge control, can serve for the restriction of the power consumption or current consumption.

FIG. 3 shows the temperature-dependent nominal resistance of an exemplary heating body such as can be used for the furnace in accordance with the invention. And indeed, the ratio of the resistance to the nominal resistance is entered in percent over the temperature in degrees Celsius. It can be recognized that the resistance has a minimum at approx. 900° C.

FIG. 4 shows the maximum Ohmic power as well as the maximum powers of the heating bodies and of the mains as well as the permitted total maximum power resulting therefrom. A mains voltage of 230 volts was selected as an example. The maximum power is entered in watts over the temperature in degrees Celsius. It can be recognized that the Ohmic power again has a maximum at 900° C. The power of the heating bodies remains constant up to a temperature of approximately 1200° C. and then drops rapidly. The power taken from the mains initially remains constant up to a temperature of approximately 500° C., then has its minimum at approximately 900° C. and then increases again to the previous level.

The allowed total maximum power behaves accordingly in that it first rises to approximately 500° C., then drops to a minimum at 900° C., rises again up to approx 1200° C. and then drops rapidly again. It can be ensured in this way that the power taken from the mains does not exceed a maximum value and that the mechanical load of the heating bodies remains in the permitted range.

The regulation via half-wave control is shown by way of example in FIG. 5. The percentage share of the half-waves applied to the heating elements 3 is given. As can be recognized, the proportion up to a temperature of approximately 1200° C. is constant at a little over 90%. The proportion up to the end temperature of approximately 1600° C. is then dropped to 30%. It is thus achieved that the power consumption is restricted in the desired manner.

FIG. 6 finally shows the voltage curve at the heating elements 3 at a mains voltage of 230 volts over the temperature. It can be recognized that the applied voltage first corresponds to the mains voltage and then drops to a relative minimum at approximately 900° C. Up to approximately 1200° C., the voltage then increases again to approximately 200 volts in order then to drop to approximately 70 volts up to the end temperature of approximately 1600° C. This voltage curve results from the half-wave control shown in FIG. 5 in conjunction with the resistance of the heating elements 3 changing in dependence on the temperature.

Alternatively to a half-wave control, a leading edge control can also be used to restrict the power consumption in the desired manner. In this respect, the strength of the heating elements 3 in dependence on the temperature can be taken into account for the control. The strength can be taken from a previously prepared table. The restriction of the power consumption by half-wave control or leading edge control can additionally take place such that the individual heating elements are acted on sequentially by a half-wave or by a part of a half-wave. This means that the three heating elements $3^1$, $3^2$ and $3^3$ are acted on sequentially. It is also possible to apply a half-wave or a part of a half-wave intermittently to each of the three heating elements $3^1$, $3^2$ and $3^3$ per se. Remaining half-waves or parts of half-waves can moreover be completely removed in that they are fed back into the mains.

The furnace can be used in a variety of ways and records excellent firing results with the furnace in accordance with the invention and the described control for the restriction of the power consumption. The furnace can in particular be used with different mains voltages, with the switching also being able to take place automatically. In addition, the described furnace has the great advantage that silicon carbide can be used for the heating elements since it can be ensured by the power restriction that it is not damaged or destroyed due to too high a power consumption.

Reference Numeral List 1 furnace housing
2 firing chamber
3 heating element
4 supply opening
5 insulation
6 housing part
7 firing table
8 firing tray
9 firing object
10 thermosensor
13 lifting plate
14 rod
19 display apparatus
20 input terminal
21 output terminal
22 relay
23 current bridge

The invention claimed is:

1. A furnace for a dental prosthesis or a partial dental prosthesis having a firing chamber, a plurality of heating elements for the heating of the firing chamber and a power supply connection for the connection of the heating elements to a mains supply,
wherein means are provided for the restriction of the power consumption of the furnace, such that a voltage applied to the furnace is determined automatically and switching between the series connection and the parallel connection of the heating elements takes place automatically, in dependence on the determined voltage.

2. A furnace in accordance with claim 1, wherein means are provided for the monitoring and for the restriction of a current consumption of the furnace.

3. A furnace in accordance with claim 1, wherein means are provided for the monitoring and restriction of the voltage effective at the heating elements for the restriction to approximately 70 to 120 volts at the individual heating element.

4. A furnace in accordance with claim 1, wherein the heating elements are connected in parallel with a voltage applied to the furnace of 115 volts ±50 volts.

5. A furnace in accordance with claim 1, wherein two to four heating elements are connected to one another in series at a voltage applied to the furnace of 230 volts ±50 volts.

6. A furnace in accordance with claim 1, wherein the switching takes place via a current bridge.

7. A furnace in accordance with claim 1, wherein the switching takes place via at least one relay.

8. A furnace in accordance with claim 1, wherein a Hall sensor is used for the current measurement.

9. A furnace in accordance with claim 1, wherein means are provided by which a current consumption and/or the voltage applied to the heating elements can be restricted in dependence on a strength of the heating elements at the currently prevailing temperature or at a maximum temperature of the heating elements.

10. A furnace in accordance with claim 9, wherein the means take the strength at the respective temperature from a previously prepared table.

11. A furnace in accordance with claim 1, wherein means are provided by which the power consumption is restricted in dependence on a permitted power removal and a current removal from the mains supply.

12. A furnace in accordance with claim 1, wherein a leading edge control or a training edge control of an AC voltage applied to the furnace is provided for the power restriction.

13. A furnace in accordance with claim 12, wherein the individual heating elements can be acted on sequentially by a half-wave or by a part of a half-wave of the applied AC current.

14. A furnace in accordance with claim 12, wherein means are provided by which the individual heating elements can have current applied intermittently per se in each case.

15. A furnace in accordance with claim 1, wherein a half-wave control of an AC voltage applied to the furnace is provided for the power restriction.

16. A furnace in accordance with claim 1, wherein the means are configured such that individual half-waves or parts of half-waves can be fully removed.

17. A furnace in accordance with claim 1, wherein the heating elements are made of silicon carbide.

18. A furnace in accordance with claim 1, wherein the heating elements are made as rods and are arranged distributed over the periphery of the firing chamber in the vertical alignment.

* * * * *